(12) United States Patent
Tulppo et al.

(10) Patent No.: US 7,953,477 B2
(45) Date of Patent: May 31, 2011

(54) DETERMINATION OF SYMPATHETIC ACTIVITY

(75) Inventors: Mikko Tulppo, Oulu (FI); Arto Hautala, Oulu (FI); Antti Kiviniemi, Oulu (FI); Hannu Kinnunen, Oulu (FI); Jukka Jaatinen, Kempele (FI)

(73) Assignee: Polar Electro Oy, Kempele (FI)

( * ) Notice: Subject to any disclaimer, the term of this patent is extended or adjusted under 35 U.S.C. 154(b) by 202 days.

(21) Appl. No.: 12/366,796

(22) Filed: Feb. 6, 2009

(65) Prior Publication Data
US 2009/0216143 A1   Aug. 27, 2009

(30) Foreign Application Priority Data

Feb. 27, 2008 (FI) .................................. 20085175

(51) Int. Cl.
*A61B 5/04* (2006.01)
(52) U.S. Cl. ..................................................... 600/519
(58) Field of Classification Search .................. 600/301, 600/495, 500, 509, 515, 519, 520, 523; 607/17
See application file for complete search history.

(56) References Cited

U.S. PATENT DOCUMENTS

| | | | |
|---|---|---|---|
| 4,625,733 A | 12/1986 | Saynajakangas | |
| 5,265,617 A | 11/1993 | Verrier et al. | |
| 5,682,901 A | 11/1997 | Kamen | |
| 2005/0065443 A1 | 3/2005 | Ternes | |
| 2005/0148895 A1 | 7/2005 | Misczynski et al. | |
| 2007/0249949 A1* | 10/2007 | Hadley | 600/519 |
| 2009/0177100 A1* | 7/2009 | Ternes | 600/509 |

OTHER PUBLICATIONS

Tulppo et al., "Physiological Background of the Loss of Fractal Heart Rate Dynamics", Circulation, Jul. 19;112(3):314-9 (2005).
Savin W.M., et al., "Autonomic Contribution to Heart Rate Recovery from Exercise in Humans", Journal of Applied Physiology: Respiratory, Environmental and Exercise Physiology, vol. 53, No. 6, p. 1572-1575 (Dec. 1982).

* cited by examiner

*Primary Examiner* — George Manuel
*Assistant Examiner* — Robert N Wieland
(74) *Attorney, Agent, or Firm* — Hoffmann & Baron, LLP

(57) ABSTRACT

An apparatus, a method and a computer program for the determination of sympathetic activity are disclosed. The method comprises: receiving heart activity data of a person; determining a recovery heart rate change speed during a recovery heart rate period in the heart activity data; and determining a sympathetic activity state of the sympathetic nervous system of the person based on the determined recovery heart rate change speed.

32 Claims, 4 Drawing Sheets

DETERMINATION OF SYMPATHETIC ACTIVITY

CROSS-REFERENCE TO RELATED APPLICATION

This application claims priority based on Finnish Patent Application No. 20085175, filed Feb. 27, 2008, which is incorporated herein by reference.

BACKGROUND

1. Field

The invention relates to an apparatus, a method and a computer program for the determination of the sympathetic activity.

2. Description of the Related Art

Stress activates the sympathetic branch of the autonomous nervous system, i.e. the higher the stress, the higher the activity state of the sympathetic nervous system. The activity state of the sympathetic nervous system may be determined by measuring the muscle sympathetic nerve activity (MSNA) of a person. MSNA can be measured reliably with a microelectrode from a peroneus nerve. This measurement is the gold standard for the sympathetic activity. The measurement can only be made invasively and in laboratory conditions, which makes it practically unsuitable for a normal person interested in exercise. Furthermore, only a few selected laboratories are capable of performing the measurement, making it practically unsuitable even for the monitoring of the day-to-day sympathetic activity of elite athletes.

SUMMARY

The present invention seeks to provide improvements on the determination of the sympathetic activity.

According to an aspect of the present invention, there is provided an apparatus comprising: an input interface configured to receive heart activity data of a person; and a processor configured to determine a recovery heart rate change speed during a recovery heart rate period in the heart activity data, and to determine a sympathetic activity state of the sympathetic nervous system of the person based on the determined recovery heart rate change speed.

BRIEF DESCRIPTION OF THE DRAWINGS

Embodiments of the present invention are described below, by way of example only, with reference to the accompanying drawings, in which.

DETAILED DESCRIPTION

The following embodiments are exemplary. Although the specification may refer to "an", "one", or "some" embodiment(s) in several locations, this does not necessarily mean that each such reference is to the same embodiment(s), or that the feature only applies to a single embodiment. Single features of different embodiments may also be combined to provide other embodiments.

Figure 1:
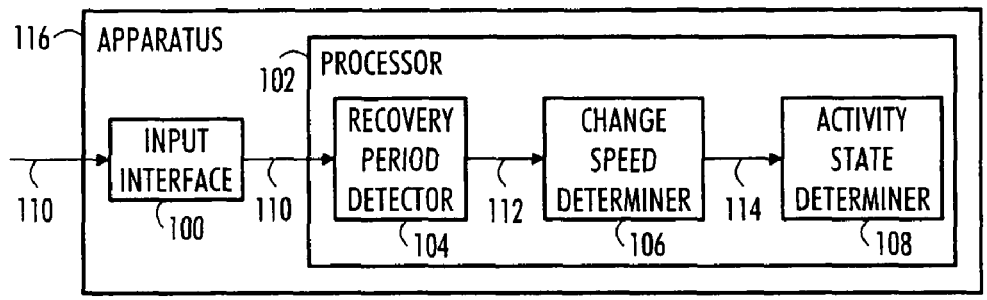
FIGS. 1, 2, 3 and 4 illustrate various embodiments of an apparatus.

FIG. 1 illustrates an apparatus 116. FIG. 1 is a simplified block diagram that only shows some elements and functional entities, all being logical units whose implementation may differ from what is shown. The connections shown in FIG. 1 are logical connections; the actual physical connections may be different. It is apparent to a person skilled in the art that the described apparatus 116 may also comprise other functions and structures. It should be appreciated that some functions, structures, and elements, and the protocols used for communication are irrelevant to the actual invention. Therefore, they need not to be discussed in more detail here. The specifications of apparatuses 116 develop rapidly. Such development may require extra changes to an embodiment. Therefore, all words and expressions should be interpreted broadly and they are intended to illustrate, not to restrict, the embodiments. Although the apparatus 116 has been depicted as one entity, different parts may be implemented in one or more physical or logical entities.

The apparatus 116 may comprise an input interface 100 configured to receive heart activity data 110 of a person. The input interface 100 may be implemented by any means enabling input in the apparatus 116. Such interface technologies include, but are not limited to, the utilization of electrical and/or magnetic fields in a wired or wireless transmission medium. A protocol for the input interface 100 may be implemented with suitable interface technologies, such as a message interface, method interface, sub-routine call interface, block interface, or any means enabling communication between functional sub-units.

The heart rate activity data may include heart rate information, beat-to-beat intervals, and/or an electrocardiogram (ECG). Although the embodiments are primarily described by using a frequency domain variable, i.e. the heart rate, in characterizing the heart activity data, a person skilled in the art is capable of implementing the embodiments by using a time-domain approach, i.e., the heart beat intervals.

Furthermore, the apparatus 116 comprises a processor 102 configured to process the received heart activity data 110 of the person. This processing may be divided into two or three operations: the processor 102 may be configured to detect 104 from the heart activity data a recovery heart rate period 112, to determine 106 a recovery heart rate change speed 114 during the recovery heart rate period 112 in the heart activity data, and to determine 108 a sympathetic activity state of the sympathetic nervous system of the person based on the determined recovery heart rate change speed 114.

The detection 104 of the recovery heart rate period is an optional feature. As explained above, the processor 102 may be configured to detect the recovery heart rate period from the heart activity data. Besides this, other ways of detecting the recovery heart rate period from the heart activity data may be used as well. The apparatus may comprise a recovery input interface (not illustrated in FIG. 1) and the processor 102 may be configured to detect the recovery heart rate period from the heart activity data on the basis of recovery input received via the recovery input interface.

The processor 102 may be a miniature electronic digital computer, which may comprise a working memory (RAM), a central processing unit (CPU), and a system clock. The CPU may comprise a set of registers, an arithmetic logic unit, and a control unit. The control unit is controlled by a sequence of program instructions transferred to the CPU from the RAM.

The control unit may contain a number of microinstructions for basic operations. The implementation of the microinstructions may vary depending on the CPU design. The program instructions may be coded using a programming language, which may be a high-level programming language, such as C, Java, etc., or a low-level programming language, such as a machine language, or an assembler. The electronic digital computer may also have an operating system, which may provide system services to a computer program written with the program instructions.

Some or all functions of the input interface 100 and the processor 102 may be implemented as a computer program comprising program instructions which, when loaded into the apparatus 116, constitute the aforementioned functionality. The computer program may be in source code form, executable form, or in some intermediate form, and it may be stored in a carrier, which may be any entity or device capable of carrying the program. Such carriers include a record medium, computer memory, read-only memory, an electrical carrier signal, a telecommunications signal, and a software distribution package, for example.

The processor 102 may be implemented as a microprocessor with software, but various hardware implementations are also feasible, such as a circuit consisting of logic components or one or more application-specific integrated circuits (ASIC). The input interface 100 and the processor 102 may be separate ASICs or integrated circuits. If necessary, there may be more than one processor 102. A hybrid of these different implementations is also feasible. When designing the implementation, a person skilled in the art will consider the requirements set for the size and power consumption of the apparatus, the necessary processing capacity, production costs, and production volumes, for example.

The apparatus 116 may be a wrist-worn portable device, a heart rate monitor, a terminal of a radio system, a personal digital assistant (PDA), or a computer, for example.

Figure 4:
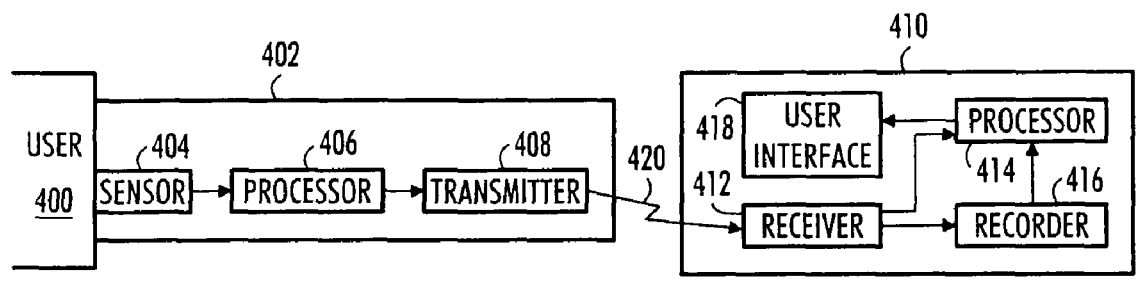
Figure 10:
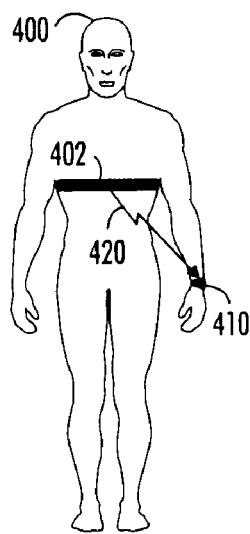
FIG. 10 illustrates another apparatus embodiment.

FIGS. 4 and 10 illustrate the implementation of the apparatus as a heart rate monitor. Polar Electro® (www.polarusa.com) designs and manufactures heart rate monitors and accessories for them. At the time of filing of this patent application, the apparatus may be implemented based on a Polar WearLink® transmitter W.I.N.D., which is a textile transmitter belt 402 worn around the chest of a user 400 and uses a 2.4-gigahertz transmitter 408 configured to transmit heart activity data 420, and on a Polar RS800sd Running Computer, which is a user interface unit 410 of the heart rate monitor and uses a receiver 412 configured to receive the heart activity data 420.

The user interface unit 410 may be worn around the wrist, like a watch, but it may well be implemented on another kind of platform, such as a subscriber terminal of a radio system: a mobile telephone for example. The user interface unit 410 may also be a sports watch for use as an instrument in sports.

The determination of the sympathetic activity in such an existing product requires relatively small and well-defined modifications: the heart activity data is measured for the heart rate determination, only the above-described processing of that data needs to be implemented. The above-defined input interface 100 may be either the sensor 404 or the receiver 412, and the above-defined processor 102 may be either a processor 406 of the transmitter belt 402 or a processor 414 of the user interface unit 410. Naturally, as the products evolve, the feasible platforms for the implementation of the embodiments described in this patent application also evolve and emerge.

In an embodiment, the input interface 100 is a computer interface, such as a proximity wireless interface or a wired interface.

In an embodiment, the input interface 100 comprises physical connectors of a computer chip, which comprises the processor 102.

Other implementations may also be possible. The heart rate monitor may also be implemented so that, instead of the solution comprising the transmitter 408 and the receiver 412, the heart rate may directly be measured from the wrist based on the pressure, for example. In such a case, the sensor 404 may be positioned against the wrist, for example. Other prior-art methods for measuring the heart rate may also be employed. As sensor technology becomes more integrated, less expensive, and its power consumption characteristics are improved, the sensor 404 may also be placed in other arrangements besides the transmitter belt 402. Polar Electro® is already marketing clothes that may be provided with separate small sensor units wirelessly communicating with the wrist unit 410.

A sensor 404 is configured to measure the heart activity of a user 400. The sensor 404 may be implemented using any technology capable of measuring an electrical or pressure signal from the skin of the user 400, for example. The processor 406 may be configured to determine the heart rate of the user 100 based on the measurements by the sensor 404.

The transmission 420 may be wireless and it may utilize the principles of time division and/or packet transmission, for example. The transmission 420 may utilize the Bluetooth® standard, or any other suitable standard/non-standard wireless communication means utilizing electric and/or magnetic fields. The proprietary radio transmission may operate at the 2.4-gigahertz or 5-kilohertz frequency, for example. Even wired transmission 420 is feasible.

A user interface 418 of the user interface unit 410 may comprise a display for the presentation. Furthermore, the user interface 418 may comprise means for producing sound and a keyboard. The display may be a liquid crystal display, for example, but it may also be implemented by any appropriate prior-art technique. The means for producing sound may be a loudspeaker or a simpler means for producing beeps or other sound signals. The keyboard may comprise a complete qwerty keyboard, a mere numeric keypad or only a few push buttons and/or rotary buttons. In addition, the user interface 418 may comprise other prior-art user interface elements, for example various means for focusing a cursor (mouse, track ball, various arrow keys, etc.), elements enabling audio control, or a touch-screen. In a wrist-worn user interface unit 410, the electronics components shown in FIG. 4 are protected by a cover (which is usually waterproof).

As explained so far, the apparatus may be a part of a heart rate monitor for measuring the user's heart rate and possibly other parameters that can be measured non-invasively (such as blood pressure). In U.S. Pat. No. 4,625,733, which is incorporated herein by reference, Säynäjäkangas describes a wireless and continuous heart rate monitoring concept where a transmitter to be attached to the user's chest measures the user's ECG-accurate (electrocardiogram) heart rate and transmits the heart rate information telemetrically to the heart rate receiver attached to the user's wrist by using magnetic coils in the transmission.

It is to be noted that when the separate transmitter belt 402 and user interface unit 410 are used, the processing of the measurements obtained from the sensor 404 may be distributed between the transmitter belt 402 and the user interface unit 410. The choice of distribution depends on the processing power and power consumption requirements, and on the transmission 420 capacity.

It is to be noted that the apparatus 116 may itself be capable of measuring the person in order to produce the heart activity data 110, as in the case with the heart rate monitor.

However, the apparatus 116 may simply receive the heart activity data 110 of the person, measured by another apparatus. Such an apparatus 116 may be implemented in a terminal of a radio system (a mobile telephone, for example), a PDA, or a computer, for example. The computer may be a personal computer (such as a desktop computer, a laptop computer, or a palmtop computer). The computer may also be a server computer. The server computer may store and process the heart activity data 110 of countless persons. The server computer may be team-specific, i.e. it is used to process the heart activity data 110 of a certain team. Alternatively, the server computer may provide heart activity data 110 storage and analysis services to a wide audience, as a worldwide web (WWW) server over the Internet, for example.

The heart activity data may be determined by a portable heart rate monitor, such as a wrist device and/or a chest unit, and delivered to the terminal of the radio system, the PDA, or the computer.

Next, with reference to FIGS. 6, 7, 8 and 9, the aforesaid detection of the recovery heart rate period, the determination of the recovery heart rate change speed and the determination of the sympathetic activity state are illustrated and compared with MSNA.

The applicant conducted experiments with two healthy subjects. They were measured with direct MSNA at rest by microneurography technique from the peroneus nerve, also their heart rate recovery after exercise was measured.

In the study, multifiber recordings of MSNA were obtained with a tungsten microelectrode inserted in the peroneus nerve. A reference electrode was placed subcutaneously at 2-3 centimeters from the recording electrode. The recording electrode was adjusted until a site was found in which muscle sympathetic bursts were clearly identified. The nerve signal was amplified (50,000 times), passed through a band-pass filter with a bandwidth of 700-2,000 hertz, and integrated with a time constant of 0.1 second. The nerve signal was also routed to an oscilloscope and a loudspeaker for monitoring throughout the study. The magnitude of sympathetic activity can be detected from an integrated signal as a number of bursts or in a more sophisticated manner as an area under the bursts (energy). MSNA measurements are described in Tulppo M P et al. Physiological background of the loss of fractal heart rate dynamics. Circulation, July 19; 112(3):314-9, 2005.

Figure 6:
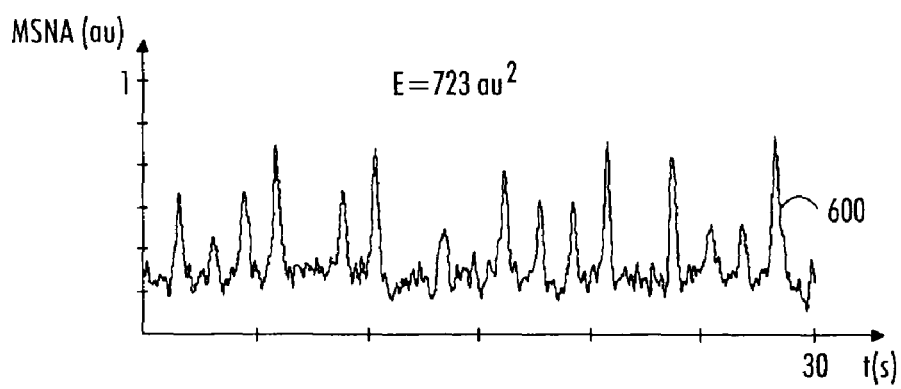
FIG. 6 illustrates MSNA measurement and FIG. 7 measurement according to the invention, both during high sympathetic activity.
Figure 7:
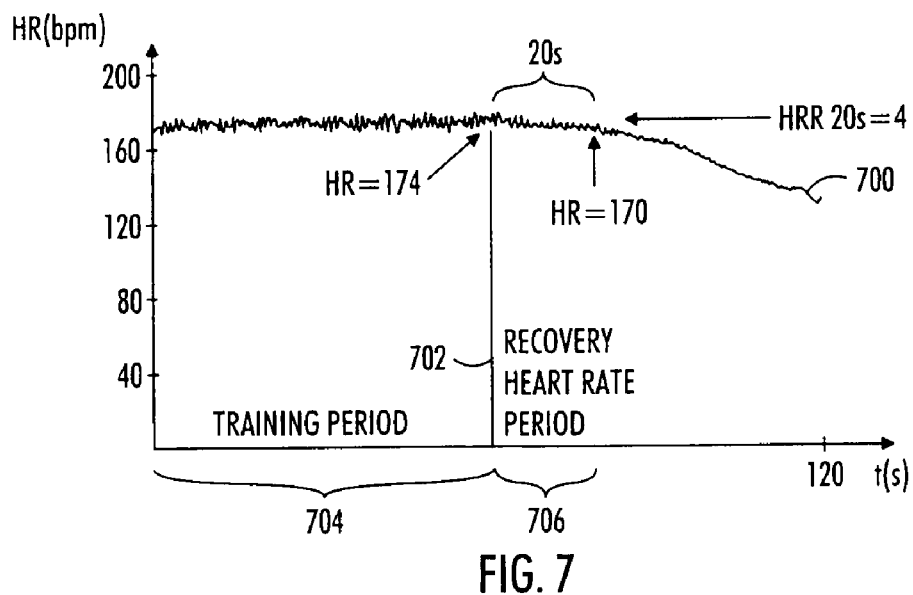

The subject of FIGS. 6 and 7 has high sympathetic activity. In FIG. 6, the measured MSNA, expressed in arbitrary units (au), is illustrated as a curve 600 over time (30 seconds). The area under the curve 600, i.e. energy, is 723 au$^2$. In FIG. 7, the subject was exercising so that the subject's heart rate was 174 beats per minute (bpm) at the end 702 of a training period 704. After the subject stopped exercising, a recovery heart rate period 706 started. As illustrated in FIG. 7, heart rate recovery (HRR) in 20 seconds was 4 bpm, from 174 bpm to 170 bpm. In other words, the heart rate change speed during the recovery heart rate period was 4 beats during the 20 seconds, or 4/20=0.2 beats/second. The processor 102 may be configured to determine the recovery heart rate change speed as a decrease of heartbeats during the recovery heart rate period, or as a decrease of heartbeats per a unit of time.

Figure 8:
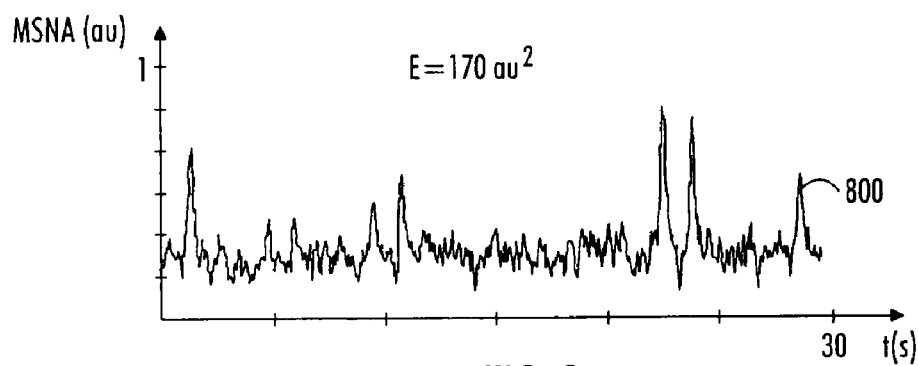
FIG. 8 illustrates MSNA measurement and FIG. 9 measurement according to the invention, both during low sympathetic activity.
Figure 9:
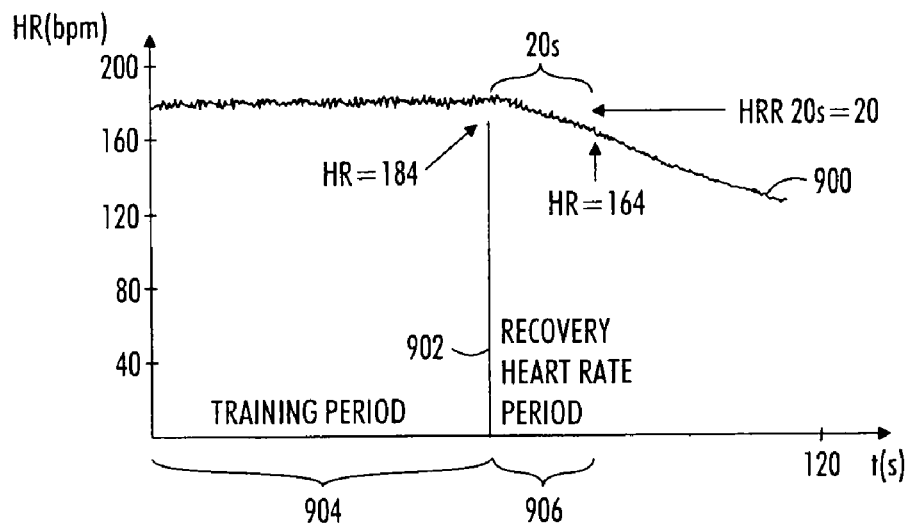

The subject of FIGS. 8 and 9 has low sympathetic activity. In FIG. 8, the area under the curve 800, i.e. energy, is 170 au$^2$. In FIG. 9, the subject was exercising so that the subject's heart rate was 184 beats per minute (bpm) at the end 902 of a training period 904. After the subject stopped exercising, a recovery heart rate period 906 started. As illustrated in FIG. 9, heart rate recovery in 20 seconds was 20 bpm, from 184 bpm to 164 bpm. In other words, the heart rate change speed during the recovery heart rate period was 20 beats during the 20 seconds, or 20/20=1 beat/second.

In mathematical terms, the heart rate change speed is a time derivative of the heart rate during the recovery heart rate period. The derivative may be an instantaneous quantity characterizing a local heart rate change, or the derivative may be an average over several heartbeats.

In the study, the duration of the recovery heart rate period was 20 seconds. The processor 102 may be configured to detect the recovery heart rate period as a fifteen to thirty-second long period, because it seems that a shorter or longer period may not give reliable results, as implied by the curves 700 and 900.

Sympathetic activity analyzed as an area under the curve is 4.3 fold higher and heart rate recovery 5.0 fold lower for the subject of FIGS. 6 and 7 compared with the subject of FIGS. 8 and 9.

A strong correlation between sympathetic activity and heart rate recovery was thus observed. The subject with a high sympathetic activity, illustrated in FIGS. 6 and 7, has a delayed heart rate recovery after exercise compared with the subject with a low sympathetic activity, illustrated in FIGS. 8 and 9, having a normal heart rate recovery after exercise. Based on this study, heart rate recovery after exercise functions as a good surrogate for sympathetic activity measurements with MSNA.

Figure 2:
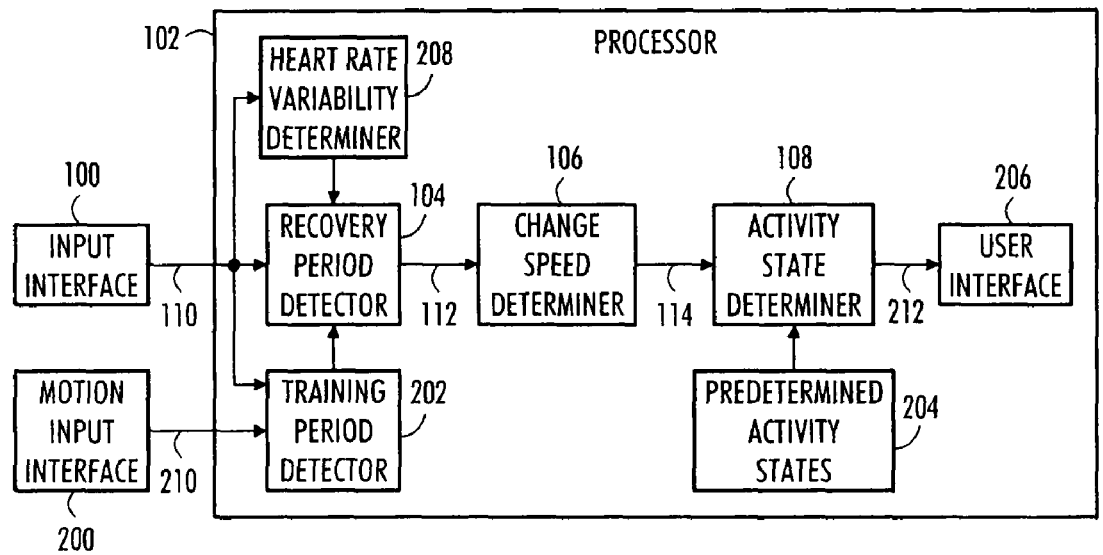

FIG. 2 illustrates further embodiments of the apparatus 116.

In an embodiment, the processor 108 is configured to store a plurality of predetermined sympathetic activity states 204. Each predetermined sympathetic activity state is associated with a predetermined range of the recovery heart rate change speed. The processor 108 is configured to determine the sympathetic activity state by checking which predetermined range of the stored sympathetic activity state corresponds to the determined recovery heart rate change speed. One implementation of this is such that the processor 102 is configured to store for a high sympathetic activity state a predetermined range having a slow recovery heart rate change speed, and for a low sympathetic activity state a predetermined range having a fast recovery heart rate change speed. If we take the values shown in FIGS. 7 and 9 as an example, we may determine two sympathetic activity states: for the high sympathetic activity state the range may be from 0 to 8 beats during the 20-second period, and for the low sympathetic activity state from the 9 beats upwards during the 20-second period. Naturally, further sympathetic activity states with their respective ranges may be determined following the principle that the height of the sympathetic activity state is inversely proportional to the recovery heart rate change speed.

In an embodiment, the apparatus 116 further comprises a user interface 206. The user interface 206 may comprise a display and/or a loudspeaker, or some other means to present visual or audio information for a human being. The processor 102 may be configured to indicate with the user interface 206 a stress level 212 of the person based on the sympathetic activity state of the sympathetic nervous system. As was explained earlier, the higher the stress, the higher the sympathetic activity state of the sympathetic nervous system. The stress level may be indicated with a textual description or with a numerical value. The textual description may use for example a three-point scale: "You have a high stress level/a normal stress level/a low stress level", or "You are stressed/normal/relaxed". The numerical values may also be expressed with a predetermined scale. The stress level may be indicated as an absolute value, or relative to the person's earlier stress level(s).

Heart rate recovery (HRR) is a well-known concept, but it appears that an automatic detection of the recovery heart rate period is an unexamined art. For that reason, still referring to FIG. 2, various embodiments relating to the automatic detection are disclosed. It is to be noted that these embodiments work quite well even for the detection of the recovery heart rate period alone, without the described use of the detected recovery heart rate period for the determination of the recovery heart rate change speed and the sympathetic activity state. In some of these embodiments, a training period is also detected 202 in connection with the heart rate recovery period.

In an embodiment, the processor 102 is configured to detect the recovery heart rate period after a training period fulfilling a predetermined condition for the heart rate. This is illustrated in FIGS. 7 and 9: after the training period 704, 904, the recovery heart rate period 706, 906 follows. The predetermined condition for the heart rate may relate to the maximum heart rate of the person or to the rest heart rate of the person. Both the actual maximum heart rate and the actual rest heart rate may easily be determined for the person, by using a heart rate monitor, for example. Another alternative is to determine either one or both of these heart rates on the basis of the person's age, for example, or on the basis of some other general rule(s) formed by a statistical analysis of a large population. One well-known rule is that the maximum heart rate of the person is obtained by subtracting the person's age in years from 220: for a 44-year old person the maximum heart rate is 220−44=176, for example.

The predetermined condition for the heart rate may vary. According to the studies of the applicant, the heart rate recovery following a training period having an intensity of 80-90% of the maximum heart rate correlates strongly (correlation 0.70-0.80) with the heart rate recovery following a training period having an intensity of 100% of the maximum heart rate. If the intensity is only 70% of the maximum heart rate, the correlation is only 0.30-0.40. The predetermined condition for the heart rate during the training period may thus be the following: the intensity must be within 80-90% of the maximum heart rate, as 100% intensity is too unpleasant and 70% intensity does not give reliable results.

Figure 11:
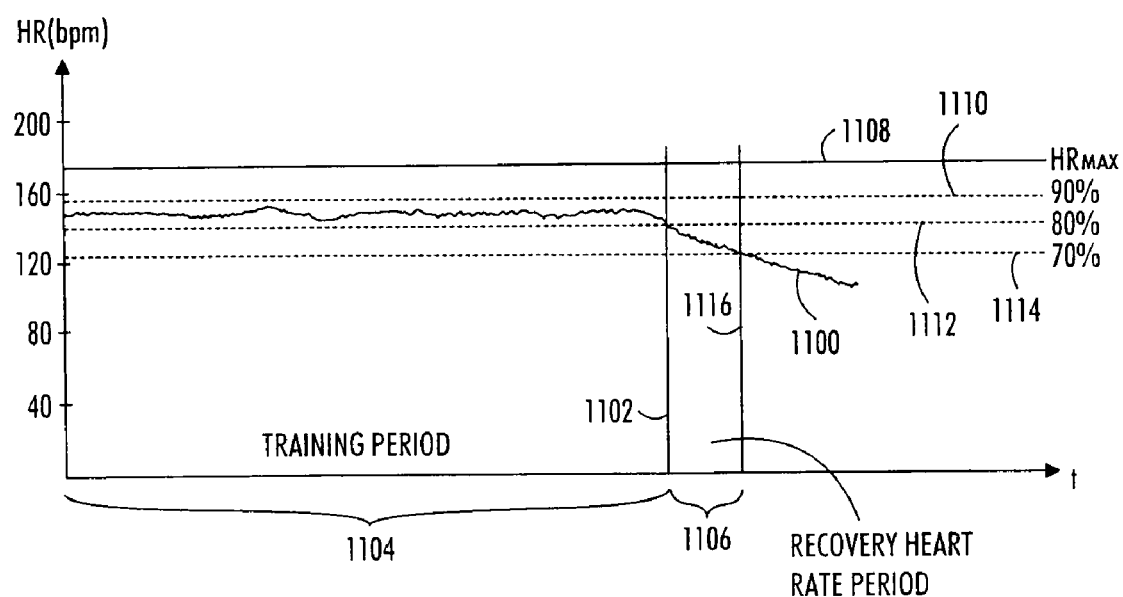
FIG. 11 illustrates detection of a recovery heart rate period.

In an embodiment illustrated in FIG. 11, the start 1102 of the heart rate recovery period 1106 is detected when the heart rate 1100 falls below an 80% limit 1112 of the person's maximum heart rate 1108. This enables the determination of the sympathetic activity state of the sympathetic nervous system after a relatively comfortable training period 1104 since the highest required heart rate level during the training period is only 80% of the person's maximum heart rate. Also a 90% limit 1110 may be used: the required exertion level is then higher, but the results may also be slightly more accurate than with the 80% limit 1112. The end 1116 of the heart rate recovery period 1106 may be detected at a 70% limit 1114 of the person's maximum heart rate. In FIG. 11, the following exemplary values are used: the maximum heart rate 1106 is 176 bpm, the 90% limit 1110 is 158 bpm, the 80% limit 1112 is 141 bpm, and the 70% limit 1114 is 123 bpm.

In an embodiment, the processor 102 is configured to detect the recovery heart rate period on the basis of the person's physical activity: during the recovery heart rate period the person's physical activity indicates a sufficiently low physical activity level. The physical activity level may indicate movements associated with the person's body.

In an embodiment, the processor 102 is configured to detect the recovery heart rate period after the training period so that the recovery heart rate period starts after the training period when the heart rate falls at a higher rate than a predetermined speed or within a predetermined time limit below a predetermined limit. One rough example: if the heart rate starts to fall and falls below 70% of the maximum heart rate within a period of two minutes, which period follows a training period having 80-90% intensity, a recovery heart rate period is detected within that two-minute period. The fast heart rate change indicates a rest or a low physical activity level, such as standing, walking or light jogging.

In an embodiment, the apparatus 116 comprises a motion input interface 200 configured to receive motion data 210 of the user. The processor 102 is configured to detect the recovery heart rate period after the training period so that the recovery heart rate period starts after the training period when the motion data 210 indicates that the person has stopped the training period. The motion data 210 comprises a number of motion pulses of the person, the speed of the person, a traveled distance of the person, a number of steps taken by the person, a step cadence of the person, a quantity describing the power of motion of the person, and a quantity describing the physical activity of the person. Such motion data 210 may be obtained from a so-called step counter using an accelerometer or pendulum to measure the motion of the user, or from a positioning device. The positioning device may operate in the Global Positioning System (GPS), the Global Navigation Satellite System (GLONASS), the Galileo Positioning System (Galileo), the Beidou Navigation System, or the Indian Regional Navigational Satellite System (IRNSS), for example. The positioning device determines its location (longitude, latitude, and altitude) using time signals transmitted along a line of sight by radio from satellites orbiting the earth. Besides global navigation satellites, the positioning device may also determine its location utilizing other known positioning techniques. It is well known that by receiving radio signals from several different base stations, the mobile phone may determine its location.

In an embodiment, the processor 102 is configured to determine 208 heart rate variability information from the heart activity data, and utilize the heart rate variability information in detecting the recovery heart rate period. The heart rate variability is a measure of the variations in heart rate. The heart rate variability information may be obtained by analyzing a time series of beat-to-beat intervals. The fact that the heart rate variability diminishes as the heart rate increases and then again increases as the heart rate decreases may be used to find out the recovery heart rate period after the training period.

In an embodiment, the apparatus 116 further comprises a recorder 416 (illustrated in FIG. 4) configured to record the heart activity data for a time period comprising at least one recovery heart rate period. The processor 102 is configured to detect the at least one recovery heart rate period utilizing a post-analysis performed for the recorded heart activity data. The post-analysis may use as its criteria for example the following: the recovery heart rate change speed exceeds a predetermined threshold. This may be implemented so that a decrease of heartbeats during a recovery heart rate period of a predetermined length exceeds the predetermined threshold.

Also other above-described ways to determine the recovery heart rate period may be used in a post-analysis fashion, and not necessarily in real-time.

Figure 3:
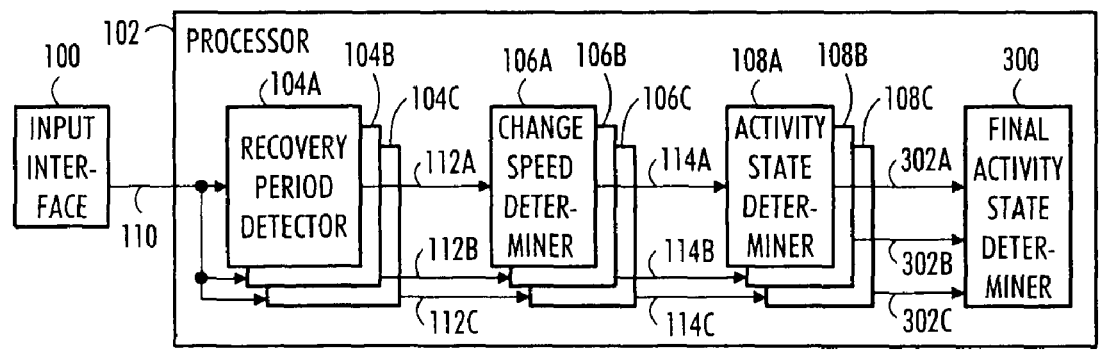

FIG. 3 illustrates another embodiment of the apparatus 116. The processor 102 is further configured to determine a plurality of recovery heart rate periods and a plurality of sympathetic activity states based on the plurality of recovery heart rate periods, and to determine the sympathetic activity state by utilizing a statistical analysis on the plurality of sympathetic activity states or by choosing the sympathetic activity state indicating the lowest sympathetic activity among the plurality of sympathetic activity states. In FIG. 3, this is implemented so that there exists a plurality of recovery period detectors 104A, 104B, 104C, which input 112A, 112B, 112C the detected recovery periods in a plurality of change speed determiners 106A, 106B, 106C, which input 114A, 114B, 114C the determined change speeds in a plurality of sympathetic activity state determiners 108A, 108B, 108C, which input 302A, 302B, 302C the determined sympathetic activity states in a final sympathetic activity state determiner 300, which determines the (final) sympathetic activity state. The statistical analysis may be applied for interval-type training, such as fitness training or games, such as football, soccer and/or ice-hockey.

In an embodiment, the processor 102 is configured to receive a command for starting the determination of a recovery heart rate change speed during the recovery heart rate period and to determine a sympathetic activity state of the sympathetic nervous system of the person based on the determined recovery heart rate change speed.

The command may be induced by a user through a user interface 206 of the apparatus 116. The user may for example inspect visually the heart activity data on a computer screen and point at an appropriate place of the curve for determining the heart rate change speed. Another possibility is for the user to use the user interface 206 in real-time during training to indicate that the training period has stopped and the recovery heart rate period starts.

In an embodiment, the apparatus 116 is coupled to fitness equipment, such as a treadmill, which reduces the training load and triggers the determination of the recovery heart rate change speed and the determination of the sympathetic activity state of the sympathetic nervous system when a sufficiently low training load is obtained.

Figure 5:
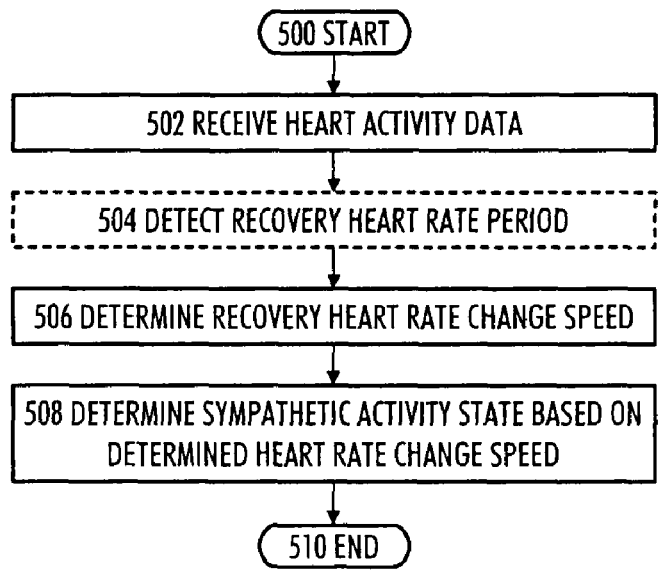
FIG. 5 is a flowchart illustrating an embodiment of a method.

Next, a method will be described with reference to FIG. 5. The operations described in FIG. 5 are in no absolute chronological order. Other functions, not described in this application, may also be executed between the operations or within the operations. Some of the operations or parts of the operations may also be left out or replaced with a corresponding operation or part of the operation. The method may be implemented as a computer program comprising computer executable instructions for causing an apparatus to perform the method. Such a computer program may be embodied on a carrier. It is to be noted that the method is not a method for treatment of the human body by therapy or a diagnostic method practiced on the human body. The determination of the sympathetic activity state of the sympathetic nervous system measures and may even record characteristics of the human body. In medical terms, stress may be defined as the disruption of homeostasis through physical or psychological stimuli. It follows from this definition that stress cannot be deemed as an illness requiring treatment. Neither can the determination of the stress level be deemed as a diagnosis, because a diagnosis is defined as the recognition of a disease by its outward signs and symptoms. Stress is not a disease; it belongs to the normal characteristics of the human body.

The method starts in 500. In 502, heart activity data of a person is received. In an optional block 504, a recovery heart rate period may be detected from the heart activity data. In 506, a recovery heart rate change speed during the recovery heart rate period in the heart activity data is determined. Finally, a sympathetic activity state of the sympathetic nervous system of the person is determined based on the determined recovery heart rate change speed in 508. The method ends in 510. The above-described embodiments of the apparatus may also be used to enhance the method.

As technology advances, the inventive concept can be implemented in various ways. The invention and its embodiments are not limited to the examples described above but may vary within the scope of the claims.

The invention claimed is:

1. An apparatus comprising:
   an input interface configured to receive heart activity data of a person; and
   a processor configured
      to determine a recovery heart rate change speed during a recovery heart rate period in the heart activity data after a training period, and
      to determine a sympathetic activity state of the sympathetic nervous system of the person before the training period based on the determined recovery heart rate change speed.

2. The apparatus of claim 1, wherein the processor is further configured to store a plurality of predetermined sympathetic activity states, each predetermined sympathetic activity state being associated with a predetermined range of the recovery heart rate change speed, and to determine the sympathetic activity state by checking which predetermined range of the stored sympathetic activity state corresponds to the determined recovery heart rate change speed.

3. The apparatus of claim 1, wherein the processor is further configured to determine a plurality of recovery heart rate periods and a plurality of sympathetic activity states based on the plurality of recovery heart rate periods, and to determine the sympathetic activity state by utilizing a statistical analysis on the plurality of sympathetic activity states or by choosing the sympathetic activity state indicating the lowest sympathetic activity among the plurality of sympathetic activity states.

4. The apparatus of claim 1, wherein the processor is further configured to automatically detect (1) the recovery heart rate period from the heart activity data, and (2) detect the recovery heart rate period from the heart activity data on the basis of a recovery input received via a recovery input interface, the apparatus comprising the recovery input interface.

5. The apparatus of claim 4, wherein the processor is further configured to automatically detect the recovery heart rate period so that the recovery heart rate period starts after a training period fulfilling a predetermined condition for the heart rate.

6. The apparatus of claim 5, wherein the predetermined condition for the heart rate relates to the maximum heart rate of the person or to the rest heart rate of the person.

7. The apparatus of claim 5, wherein the processor is further configured to automatically detect the recovery heart rate period after the training period so that the recovery heart rate period starts after the training period when the heart rate falls at a higher rate than a predetermined speed or within a predetermined time limit below a predetermined limit.

8. The apparatus of claim 5, wherein the apparatus further comprises a motion input interface configured to receive motion data of the user, and the processor is further configured to detect the recovery heart rate period after the training period so that the recovery heart rate period starts after the training period when the motion data indicates that the person has stopped the training period.

9. The apparatus of claim 4, wherein the processor is further configured to determine heart rate variability information from the heart activity data, and utilize the heart rate variability information in detecting the recovery heart rate period.

10. The apparatus of claim 4, wherein the apparatus further comprises a recorder configured to record the heart activity data for a time period comprising at least one recovery heart rate period, and the processor is further configured to detect the at least one recovery heart rate period utilizing a post-analysis performed for the recorded heart activity data.

11. The apparatus of claim 1, wherein the apparatus further comprises a user interface, and the processor is further configured to indicate, with the user interface, a stress level of the person, the stress level being determined using the sympathetic activity state of the sympathetic nervous system.

12. The apparatus of claim 1, wherein the apparatus further comprises a user interface, and the processor is further configured to indicate, with the user interface, a stress level of the person based on the sympathetic activity state of the sympathetic nervous system.

13. The apparatus of claim 1, wherein the processor is further configured to automatically detect the recovery heart rate period as a fifteen to thirty-second long period from the end of the training period.

14. The apparatus of claim 1, wherein the processor is further configured to automatically detect the recovery heart rate period after a training period fulfilling a predetermined condition for the heart rate, the predetermined condition for the heart rate during the training period being within 80-90% of the maximum heart rate.

15. The apparatus of claim 1, wherein the processor is further configured to automatically detect the end of the heart rate recovery period at a 70% limit of the person's maximum heart rate.

16. The apparatus of claim 1, wherein the recovery heart rate period starts immediately after the person stops exercising, the sympathetic activity state being associated with a predetermined range of values of the recovery heart rate change speed.

17. A method comprising:
receiving heart activity data of a person;
determining a recovery heart rate change speed during a recovery heart rate period in the heart activity data after a training period; and
determining a sympathetic activity state of the sympathetic nervous system of the person before the training period based on the determined recovery heart rate change speed.

18. The method of claim 17, further comprising:
storing a plurality of predetermined sympathetic activity states, each predetermined sympathetic activity state being associated with a predetermined range of the recovery heart rate change speed; and
determining the sympathetic activity state by checking which predetermined range of the stored sympathetic activity state corresponds to the determined recovery heart rate change speed.

19. The method of claim 17, further comprising:
determining a plurality of recovery heart rate periods and a plurality of sympathetic activity states based on the plurality of recovery heart rate periods; and
determining the sympathetic activity state by utilizing a statistical analysis on the plurality of sympathetic activity states or by choosing the sympathetic activity state indicating the lowest sympathetic activity among the plurality of sympathetic activity states.

20. The method of claim 17, further comprising at least one of
(1) detecting the recovery heart rate period from the heart activity data, and
(2) detecting the recovery heart rate period from the heart activity data on the basis of received recovery input.

21. The method of claim 20, further comprising:
detecting the recovery heart rate period after a training period fulfilling a predetermined condition for the heart rate.

22. The method of claim 21, wherein the predetermined condition for the heart rate relates to the maximum heart rate of the person or to the rest heart rate of the person.

23. The method of claim 21, further comprising:
detecting the recovery heart rate period after the training period so that the recovery heart rate period starts after the training period when the heart rate falls at a higher rate than a predetermined speed or within a predetermined time limit below a predetermined limit.

24. The method of claim 21, further comprising:
receiving motion data of the user; and
detecting the recovery heart rate period after the training period so that the recovery heart rate period starts after the training period when the motion data indicates that the person has stopped the training period.

25. The method of claim 20, further comprising:
determining heart rate variability information from the heart activity data; and
utilizing the heart rate variability information in detecting the recovery heart rate period.

26. The method of claim 20, further comprising:
recording the heart activity data for a time period comprising at least one recovery heart rate period; and
detecting the at least one recovery heart rate period utilizing a post-analysis performed for the heart activity data.

27. The method of claim 17, further comprising:
indicating a stress level of the person based on the sympathetic activity state of the sympathetic nervous system.

28. The method of claim 17, wherein the recovery heart rate period starts immediately after the person stops exercising, the sympathetic activity state being associated with a predetermined range of values of the recovery heart rate change speed.

29. A non-transitory computer-readable storage medium comprising instructions that, when executed by a processing device, cause the processing device to:
receive heart activity data of a person;
determine a recovery heart rate change speed during a recovery heart rate period in the heart activity data after a training period; and
determine a sympathetic activity state of the sympathetic nervous system of the person before the training period based on the determined recovery heart rate change speed.

30. The non-transitory computer-readable storage medium of claim 29, further comprising instructions that, when executed by a processing device, cause the processing device to:
store a plurality of predetermined sympathetic activity states, each predetermined sympathetic activity state being associated with a predetermined range of the recovery heart rate change speed; and determine the sympathetic activity state by checking which predetermined range of the stored sympathetic activity state corresponds to the determined recovery heart rate change speed.

31. The non-transitory computer-readable storage medium of claim 29, further comprising instructions that, when executed by a processing device, cause the processing device to:

indicate a stress level of the person based on the sympathetic activity state of the sympathetic nervous system.

32. The apparatus of claim 29, wherein the recovery heart rate period starts immediately after the person stops exercising, the sympathetic activity state being associated with a predetermined range of values of the recovery heart rate change speed.

* * * * *